United States Patent [19]

Lang

[11] 4,013,742

[45] Mar. 22, 1977

[54] DEVICE FOR WETTING AND HEATING GASES, PREFERABLY BREATHING GASES IN RESPIRATORS

[76] Inventor: Volker Lang, 8012 Spitzwegstr. 63 b, Ottobrunn, Germany

[22] Filed: July 28, 1975

[21] Appl. No.: 599,478

[30] Foreign Application Priority Data

July 29, 1974 Germany ............................ 2436406

[52] U.S. Cl. .............................. 261/130; 122/5.5 R; 128/192; 128/201; 219/10.49; 219/275; 261/142; 261/153; 261/121 R; 261/DIG. 65

[51] Int. Cl.² ...................... B01F 3/04; A61M 15/00

[58] Field of Search .......... 261/129, 130, 131, 142, 261/151–153, 121 A, DIG. 31, 109, 110, 112, DIG. 65; 219/10.49, 10.51, 10.79, 362, 275; 128/185–187, 192, 201, 205, 208, 212; 122/5.5 A, 209 A, DIG. 7

[56] References Cited

UNITED STATES PATENTS

| | | | |
|---|---|---|---|
| 2,166,574 | 7/1939 | Adolphsen | 261/122 X |
| 2,522,718 | 9/1950 | Huck | 128/192 X |
| 3,440,384 | 4/1969 | Schroeder | 219/10.49 |
| 3,659,604 | 5/1972 | Melville et al. | 128/212 |
| 3,806,102 | 4/1974 | Valenta et al. | 261/142 |
| 3,864,440 | 2/1975 | Giocoechea | 261/142 X |

Primary Examiner—Frank W. Lutter
Assistant Examiner—William A. Cuchlinski, Jr.
Attorney, Agent, or Firm—Howard C. Miskin

[57] ABSTRACT

In a humidifying and heating apparatus for respiratory gas, a transformer for inductively heating a humidifying liquid is provided in a housing having a socket, whilst a vessel for containing the liquid is made as a separable sterilizable or disposable unit through which the respiratory gas can be passed and which has a plug connector releasably engaged in the socket. The secondary transformer winding is in the form of a plate which is disposed in the plug connector and comprises an upper portion in contact with the liquid and a lower portion straddling the transformer core.

10 Claims, 4 Drawing Figures

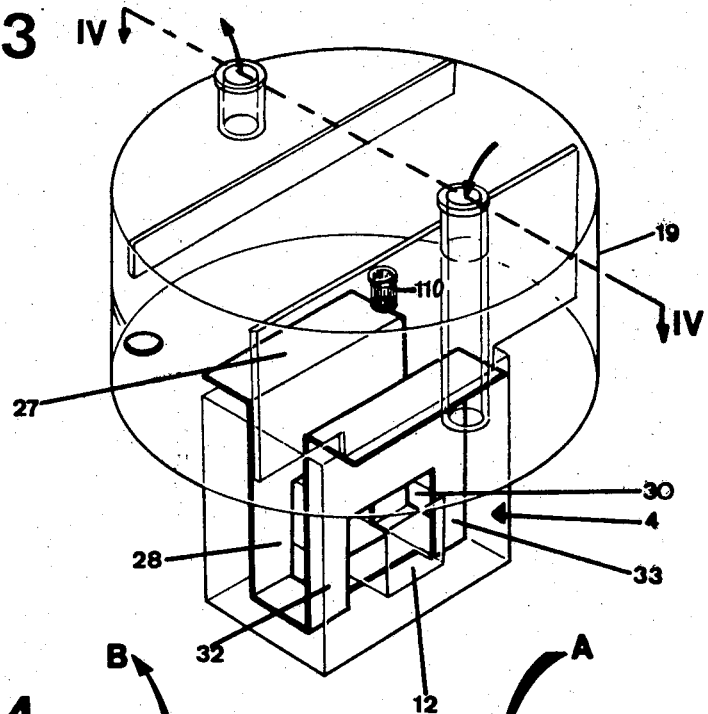
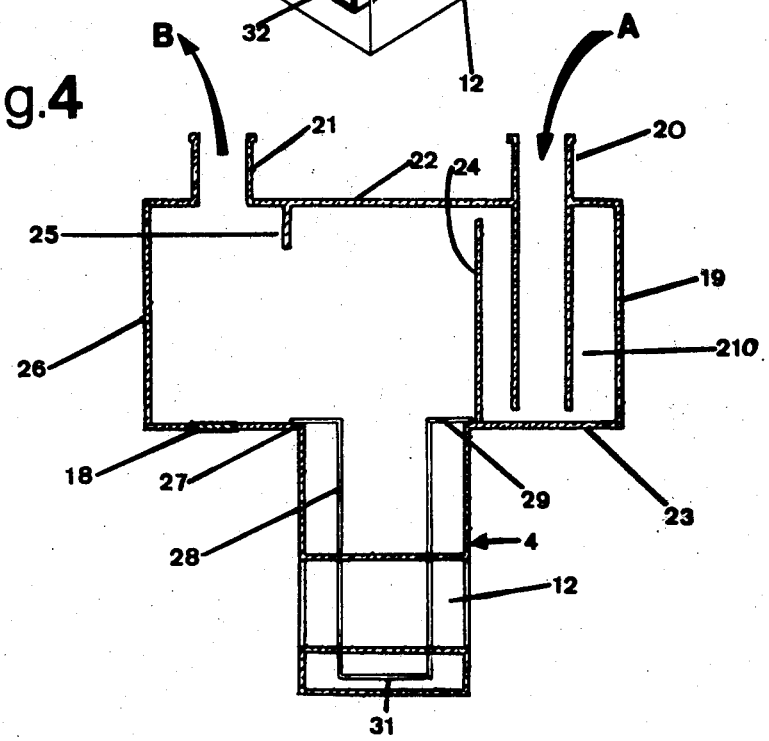

DEVICE FOR WETTING AND HEATING GASES, PREFERABLY BREATHING GASES IN RESPIRATORS

INTRODUCTION

The invention relates to humidifying and heating apparatus for respiratory gas.

In recent years, improved artificial respirators have resulted in a marked reduction in the mortality rate of babies, accident victims and heart surgery patients. However, there are still problems to be overcome with regard to satisfactory sterilizaton of the respirator components and the maintenance and operation of respirators without the need for returning them to a service centre.

The importance of effective sterilization is exemplified by pneumonia caused by unhygienic respirators, where the mortality rate is still 80 to 90% for new born babies, despite modern antibiotic treatment facilities.

I have found that the humidifying and heating apparatus of respirators is the main source of infection. The principal medical requirements for this apparatus in a respirator are:

1. High bacteriological safety (that is to say the possiblity of sterilization or disinfection by simple expedients or a design providing a disposable apparatus.
2. Accurate selectability of the temperature for the respiratory gas.
3. Optimum humidifcation of the respiratory gas.
4. Ease of manipulation by nursing staff to minimize life-endangering mistakes.

Currently marketed apparatus does not meet all of these requirements, the principal difficulty that is experienced being with the hygienic requirements.

SUMMARY OF INVENTION

It is an object of the present invention to provide a safe humidifying and heating apparatus that is easy to handle, keeps sterile and produce economically.

Accordingly, the invention provides a humidifying and heating apparatus for respiratory gas, comprising a transformer for inductively heating a humidifying liquid, and a vessel for containing said liquid and provided with an inlet and an outlet for said gas, wherein said transformer comprises a magnetic core having first and second legs and disposed in a housing, said first leg carrying a primary coil and said housing being formed with a socket, and wherein said vessel comprises a depending extension defining a plug connector releasably engageable in said housing socket, a secondary winding of said transformer being formed by a plate which is mounted in said plug connector and has an upper portion in contact with said liquid and a lower portion adapted to straddle said second leg when said plug connector is engaged in said socket.

The invention is based on the concept of accommodating the relatively expensive components of the humidifying and heating apparatus in a control box and providing the easily sterilizable components as a detachable separate unit of which the vessel for the humidifying liquid is so cheap that it can even be disposable after a single instance of use.

DESCRIPTION OF VIEWS OF DRAWINGS

An example of a humidifying and heating apparatus according to the invention is illustrated in the accompanying drawings, wherein:

FIG. 3 is an enlarged diagrammatic perspective view of the vessel alone, and

FIG. 4 is a section on the line IV—IV in FIG. 3.

DETAILED DESCRIPTION

Figure 2:
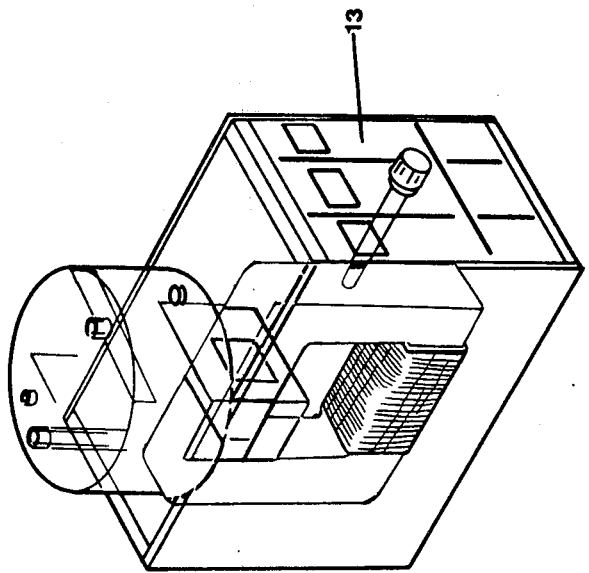
FIG. 2 is a diagrammatic perspective view of the assembled apparatus.
Figure 1:
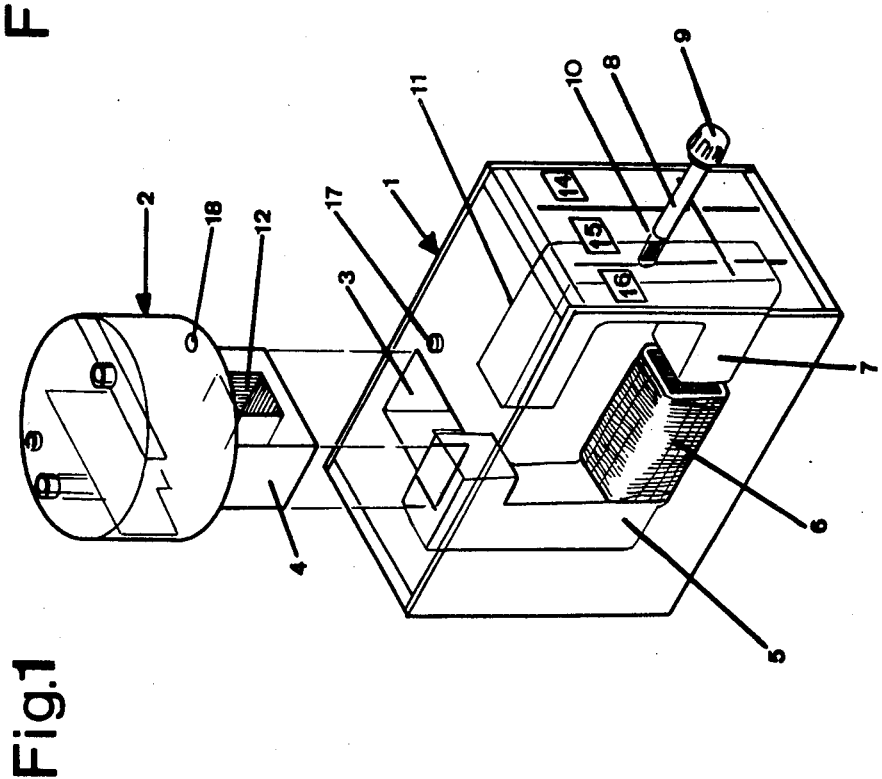
FIG. 1 is a diagrammatic perspective exploded view of the vessel for humidifying liquid and the control box unit.

The illustrated humidifying and heating apparatus comprises two principal components 1 and 2 which are detachably securable to one another in a manner to be described. The component 1 is in the form of a housing containing comparatively expensive heating, controlling and indicating equipment which can to advantage be re-used many times because it does not come into contact with either the respiratory gas or the humidifying liquid therefor and can thus not be a source of contamination. The component 2 is in the form of a vessel for containing sterilized humidifying liquid to be brought into contact with the respiratory gas and the interior of the vessel must therefore be scrupulously clean. Since the vessel 2 is detachable from the housing 1, it can either be entirely replaceable, i.e. disposable, in which case each replacement vessel will already contain humidifying liquid that has been introduced to the vessel under the strictly sterile conditions obtaining in the factory or the labratory, or one and the same vessel can be subjected to sterilization and refilling by the user after each occasion of use. The simplicity and ease with which the two components are detachable and connectible by means of the invention and the utter simplicity of the liquid vessel (which makes it cheap to produce and/or very easy to sterilize), for the first time makes it possible to employ a humidifying and heating apparatus in the manner indicated, without in any way departing from the rigid clinical conditions that are imposed on medical equipment.

The top of the housing 1 is provided with an aperture defining a rectangular shaft or socket 3 for receiving a parallelepiped plug connector 4 depending from the vessel 2. Inductive heating of the humidifying liquid in the vessel 2 is effected by means of a transformer of which the core-type magnetic yoke 5 is disposed in the housing 1. This yoke or core 5 is not only laminated in conventional manner but is constructed in two U-shaped sections which can be temporarily moved apart and each of which forms part of a first leg 7 and a second leg 11.

When the core sections are locked together, the first leg 7 is surrounded by a primary transformer winding or coil 6 and the second leg 11 is straddled by at least one channel-section plate 28 which constitutes a low-ohmic secondary short circuit winding and is housed in the plug connector 4. One of the transformer core sections is fixed in the housing 1; the other section is displaceable by means of a rod 8 having an actuating knob 9 and projecting through a hole 10 in the housing. When moved apart, the core sections define in the leg 11 a gap which is disposed beneath the socket 3 and permits the plug connector 4 of the vessel 2 to be pushed home. When the core sections are locked together by the rod 8, which may be screw-threaded, and the plug connector 4 is in position, the leg 11 extends through a rectangular tunnel 12 formed by a transverse hole in the plug connector and the magnetic circuit of the transformer core is closed.

The front 13 of the housing 1 is equipped with various other control and indicating devices, for example indicators 14, 15, 16 for temperature, oxygen content of the respiratory gas and respiratory pressure, as well as preselector buttons for these parameters but these are incidental to the present invention, as are a temperature sensing button 17 on the housing for making contact with a small metal disc 18 of the vessel 2.

The vessel 2 for humidifying liquid comprises a cylindrical wall 19 of transparent plastics material and supporting a circular upper wall 22 and an annular base 23 carrying at its inner periphery a depending projection that forms the aforementioned plug connector 4. The upper wall 23 contains an inlet 20 connectible to a source of respiratory gas by a sterile flexible tube (not shown) which may be disposable, an outlet 21 which is also connectible to a sterile flexible tube (not shown) for withdrawing humidified gas from the vessel, and a liquid filling aperture closable by a runner stopper 110. The liquid can be replenished through this last-mentioned aperture without stopping the respirator. The aforementioned plug connector 4 is, as already mentioned, formed by an extension of the vessel 2 depending from the centre of the annular base 23 and provided with the aforementioned tunnel 12 and channel-section plate or secondary transformer winding 28. Liquid contained in the vessel 2 is also in contact with an upper portion of the plate 28 within the extension or plug connector 4 but of course only as far as an unreferenced transverse wall bounding the top of the tunnel 12.

The upper ends of the limbs of the channel-section plate 28 carry flanges 27, 29 secured to the base 23. The base 31 of the plate 28 and both limbs of this plate are recessed to form transverse rectangular apertures 30 aligned with the tunnel 12 so that, when the plug connector 4 is engaged in the socket 3 and the transformer sections have been brought together, the limb portions 32, 33 of the plate 28 straddle the leg 11 of the transformer core 5, the leg 11 being disposed in the tunnel 12. It will now be evident that liquid in contact with the plate 28 will be inductively heated thereby when the primary coil 6 is energized.

The heated liquid is of course swirled around the vessel under convection currents, assisted also by a circuitous path provided in the vessel for the respiratory gas with which is is to be brought into direct intimate contact so that the gas will be humidified as well as heated by the liquid. For this purpose a tube 210 depends from the upper wall 22 of the vessel in registry with the gas inlet 20 and stops closely above the base 23. A first baffle plate 24 extends upwardly from the base 23 between the tube 210 and the inner periphery of the base and stops 2 to 5 mm short of the upper wall 22. A second baffle plate 25 depends a short distance from the upper wall 22 at a location between the baffle plate 24 and the gas outlet 21. Both baffle plates 24, 25 extend along chords of the cylindrical wall 19 and contact same with their ends. The baffle plate 24 may contain slots. The outside of the transparent wall 19 is provided with a marker 26 to indicate the level to which the vessel 2 should be filled with humidifying liquid, namely so that the surface of the liquid will be disposed below the lower end of the baffle plate 25 and below the upper end of the baffle plate 24 but above the lower end of the tube 210.

Only after the plug and socket connection 3, 4 has been made between the vessel 2 and housing 1, and the transformer core sections have been locked together by operating the rod 8, is the transformer ready to be energised to heat the humidifying liquid by inductive heating. Respiratory gas entering through the inlet 20 first makes contact with the heated humidifying liquid at the lower end of the tube 210. The stream of gas is divided up on striking the base 23 of the vessel and bubbles past the surface of the liquid at the right-hand side of the baffle plate 24, the liquid surface being substantially at the level of the marker 26. The gas then passes over the top of the baffle plate 24 and is redirected towards the liquid surface by the baffle plate 25 before leaving through the gas outlet 21. The circuitous path thus provided for the respiratory gas through the vessel 2 primarily serves to prolong the residence time of the respiratory gas, i.e. to give the liquid sufficient time to humidify and heat the gas. The secondary transformer winding or plate 28 can emit up to 300 W of heat by induction. Even with a gas velocity as low as 80 liters/minute, one can obtain humidification from 90 to 100% and accurate heating to the required temperature (usually body temperature of 36° C), the inductive heating means as described being most suitable for this purpose.

If the vessel 2 of the apparatus is to be re-used, corrosion-resistant ferromagnetic material must be employed for the or each plate 28 and the vessel must be regularly cleaned. Rinsing out may suffice because the interior of the vessel is very simply constructed and readily accessible by the rinsing liquid. If sterilization by means of steam is preferred, a steam sterilizer would comprise an inductive heating transformer in a socketed housing and functioning in much the same way as does the transformer in the housing 1 of the humidifier. For sterilizing purposes, the vessel is half filled with sterilized water, plugged into the sterilizer housing and left for the water to boil and form steam which penetrates throughout to sterilize all portions of the vessel that were formerly in contact with respiratory gas. The steam can be vented through both of the apertures 20, 21 and the preferably silicone rubber flexible tubes connected thereto, so that these tubes are likewise disinfected and need not be handled (with consequential risk of contamination) when the vessel 2 is subsequently reconnected to the housing 1 for use as a humidifier as previously described.

Provision may be made to monitor the apparatus and protect it against running dry. The principle that is employed is that the ohmic resistance of the secondary winding or plate 28 increases on overheating. This causes not only the secondary current but also the primary current to fall. This reduced primary current can be utilised in conjunction with the voltage drop across a given resistance to control an electronic safety unit which is known per se.

Another known expedient that can be employed is a temperature-sensitive semi-conductor in a control circuit which determines the current consumption of the transformer and thus the heat output of the transformer secondary. For reasons of hygiene, the actual temperature of the liquid in the vessel 2 can be measured with sufficient accuracy by means of the aforementioned temperature sensing button 17 on the housing 1 making contact with the metal disc 18 on the outside of the vessel 2. When the temperature deviates from a nominal value, it can be controlled by an adjustable electronic thermostat giving a continuous temperature reading as well as an audible alarm.

Apart from being protected against running dry, it may be desirable to indicate the water level not only visually (because the wall 19 of the vessel 2 is transparent), but also by means of a known reflecting light barrier with pulsed light.

Further, the oxygen content in the respiratory gas may be continuously or intermittently indicated with the aid of warning lights in a manner that is known in this art.

If a bacteria filter as known in the art is attached to the apparatus hereinbefore described, bacterial contamination as caused by the respirator can to a large extent be eliminated. Hygienic safety is even further enhanced by using sterile disposable tubes for connection to the inlet 20 and outlet 21. If the vessel 2 is to be disposable, it can be made from polystyrene, polyethylene, polyvinylchloride or polypropylene, which are relatively cheap plastics that can be fabricated by injection moulding or by blow moulding with subsequent welding. For multiple use, the material of the vessel preferably comprises a synthetic organic polymer such as polycarbonate or possibly polyamide or polypropylene. Whilst a material such as polycarbonate considerably increases the cost of the vessel, its temperature resistance permits steam sterilization in a manner hereinbefore described.

I claim:

1. Humidifying and heating apparatus for respiratory gas, comprising a transformer for inductively heating a humidifying liquid, and a vessel for containing said liquid and provided with an inlet and an outlet for said gas, wherein said transformer comprises a magnetic core having first and second legs and disposed in a housing, said first leg carrying a primary coil and said housing being formed with a socket, and wherein said vessel comprises a depending extension defining a plug connector releasably engageable in said housing socket, a secondary winding of said transformer being formed by a plate which is mounted in said plug connector and has an upper portion in contact with said liquid and a lower portion adapted to straddle said second leg when said plug connector is engaged in said socket.

2. Humidifying and heating apparatus for respiratory gas, comprising a transformer for effecting inductive heating of a humidifying liquid, a housing, an aperture defining a socket in the top of said housing, a magnetic core of said transformer being disposed in said housing, said core being constructed in two sections each forming part of first and second legs of said core, a primary coil for said transformer disposed around said first leg of said core, means for temporarily separating said core sections whereby to form a closable gap in said second leg beneath said socket, a vessel for containing said humidifying liquid, an inlet in said vessel for introducing respiratory gas to come into intimate contact with said humidifying liquid, an outlet in said vessel for withdrawing humidified said respiratory gas, said vessel including a depending extension defining a plug connector which is releasably engageable in said socket when said gap in said second leg is open, a transverse hole in said plug connector defining a tunnel in registry with said second leg, and a secondary winding for said transformer in the form of at least one channel-section plate having limbs mounted in said plug connector so as to be in contact with said humidifying liquid, said limbs being provided with transverse apertures aligned with said tunnel whereby, when said plug connector is engaged in said socket and said gap in said second leg is closed, said plate limbs straddle said second leg which is received in said tunnel.

3. Apparatus according to claim 2, wherein one of said transformer core sections is stationarily mounted in said housing and the other section is dislaceably mounted, said separating means comprising a manually operable rod which is connected to said other core section and extends through a hole in said housing.

4. Apparatus according to claim 2, including temperature sensing means at the top of said housing and a metal plate on the underside of said vessel making contact with said sensing means when said plug connector is engaged in said socket.

5. Apparatus according to claim 2, wherein said vessel comprises a cylindrical side wall, a circular upper wall supported by said side wall and provided with said inlet and said outlet, and an annular base formed with said depending extension.

6. Apparatus according to claim 5, wherein said vessel is made from transparent plastic material.

7. Apparatus according to claim 5, wherein said inlet communicates with a tube extending into said vessel from said upper wall and terminating short of said base.

8. Apparatus according to claim 5, wherein a baffle plate disposed between said inlet and outlet upstands from said vessel base and terminates short of said upper wall.

9. Apparatus according to claim 5, wherein a baffle plate disposed between said inlet and outlet depends a short distance from said upper wall.

10. Apparatus according to claim 5, including a closable filling aperture in said upper wall, a tube depending from said upper wall in registry with said inlet and terminating closely above said base, a first baffle plate upstanding from said base adjacent said tube and having its upper end spaced from said upper wall, a second baffle plate depending from said upper wall between said first baffle plate and said outlet and having its lower end spaced from said base, and a marker provided on said side wall above said base and below the level of said ends of said first and second baffle plates.

* * * * *